(12) United States Patent
Towe et al.

(10) Patent No.: US 10,818,404 B2
(45) Date of Patent: Oct. 27, 2020

(54) METHODS AND SYSTEMS FOR DETERMINING THE SHAPE OF A RADIOTHERAPY BEAM

(71) Applicant: Elekta Limited, West Sussex (GB)

(72) Inventors: Stephen Towe, Sydney (AU); Begoña Vivas-Maiques, Amsterdam (NL); Janusz Harasimowicz, West Sussex (GB); David Roberts, West Sussex (GB)

(73) Assignee: Elekta Limited, West Sussex (GB)

( * ) Notice: Subject to any disclaimer, the term of this patent is extended or adjusted under 35 U.S.C. 154(b) by 0 days.

(21) Appl. No.: 16/212,078

(22) Filed: Dec. 6, 2018

(65) Prior Publication Data

US 2019/0175944 A1 Jun. 13, 2019

(51) Int. Cl.
*A61N 5/10* (2006.01)
*G21K 1/04* (2006.01)

(52) U.S. Cl.
CPC .......... *G21K 1/046* (2013.01); *A61N 5/1045* (2013.01); *A61N 5/1067* (2013.01)

(58) Field of Classification Search
CPC .. A61N 5/1045; A61N 5/1075; A61N 5/1048; G01T 1/29; G21K 1/046
See application file for complete search history.

(56) References Cited

U.S. PATENT DOCUMENTS 4,882,741 A * 11/1989 Brown ................. A61N 5/1042
378/152
5,144,647 A 9/1992 Kikuchi
5,166,531 A 11/1992 Huntzinger
(Continued)

FOREIGN PATENT DOCUMENTS

| EP | 2090333 A2 | 8/2009 |
|---|---|---|
| EP | 2359905 A1 | 8/2011 |
| WO | WO 2008/141667 A1 | 11/2018 |

OTHER PUBLICATIONS

Patel, I., A. G. Glendinning, and M. C. Kirby. "Dosimetric characteristics of the Elekta Beam Modulator™." Physics in Medicine & Biology 50.23 (2005): 5479 (Year: 2005).*
(Continued)

*Primary Examiner* — Wyatt A Stoffa
(74) *Attorney, Agent, or Firm* — Finnegan, Henderson, Farabow, Garrett & Dunner LLP (57) ABSTRACT

A method of determining the shape of a radiation beam of a radiotherapy system at a treatment position, the system comprising a radiation source and a multi-leaf collimator disposed between the radiation source and the treatment position. The multi-leaf collimator includes an array of moveable leaves positioned to intersect and block parts of the radiation beam to define the shape of the radiation beam at the treatment position. The leaves of a group are aligned such that the planes of the leaves in that group converge at a point displaced laterally from the radiation source. The method includes, for each leaf in the array positioned to intersect the radiation beam, determining a projected width with respect to the radiation beam, the projected width being greater than the thickness of the respective leaf, and using the projected leaf width to determine the shape of the radiation beam at the treatment position.

17 Claims, 7 Drawing Sheets

(56) References Cited

U.S. PATENT DOCUMENTS

| | | | | |
|---|---|---|---|---|
| 6,167,114 | A * | 12/2000 | Siochi | A61N 5/1031 |
| | | | | 378/62 |
| 6,473,490 | B1 * | 10/2002 | Siochi | A61N 5/103 |
| | | | | 378/65 |
| 6,853,705 | B2 * | 2/2005 | Chang | G21K 1/046 |
| | | | | 378/65 |
| 7,583,775 | B2 * | 9/2009 | Ozaki | G21K 1/04 |
| | | | | 250/370.11 |
| 7,697,662 | B2 * | 4/2010 | Maltz | A61N 5/1048 |
| | | | | 378/147 |
| 8,067,751 | B2 * | 11/2011 | Mohr | A61N 5/1042 |
| | | | | 250/492.1 |
| 2012/0068087 | A1 * | 3/2012 | Mohr | G21K 1/04 |
| | | | | 250/492.1 |
| 2015/0273239 | A1 | 10/2015 | Hsu et al. | |
| 2018/0154179 | A1 * | 6/2018 | Ollila | A61N 5/1065 |
| 2019/0001156 | A1 * | 1/2019 | Tulik | A61N 5/1039 |
| 2019/0126070 | A1 * | 5/2019 | Hsieh | A61N 5/1049 |

OTHER PUBLICATIONS

International Search Report for corresponding GB Application No. 1720403.3, filed Dec. 7, 2017 (dated May 11, 2018).

Tacke, M. et al. "6MV dosimetric characterization of the 160 MLC, the new Siemens multileaf collimator." Medical Phys. vol. 35, No. 5 (Apr. 2008): 1634-1642.

International Search Report for European Patent Application No. EP 18 21 0886.0, dated Jun. 11, 2019.

* cited by examiner

METHODS AND SYSTEMS FOR DETERMINING THE SHAPE OF A RADIOTHERAPY BEAM

CROSS-REFERENCE TO RELATED APPLICATION

This application claims the benefit and priority of prior United Kingdom Patent Application No. 1720403.3, filed on Dec. 7, 2017, the entire contents of which are incorporated by reference herein.

FIELD OF THE INVENTION

The invention relates to the determination of the shape of a radiotherapy beam at a target position. In particular, the invention provides methods for determining the effect of the leaves of a multi-leaf collimator on the radiation pattern projected onto a tumour (target) of a patient.

BACKGROUND ART

In radiotherapy, a beam of x-rays is directed at a target to be treated in a patient. The objective of radiotherapy is to attempt to irradiate the target, typically a tumour located on or in the body of a patient, with sufficient radiation to shrink the tumour while minimizing irradiation and damage of surrounding healthy tissue. One way to achieve this is to introduce a beam shaper or collimator between the x-ray source and the patient. The collimator blocks parts of the beam so that the shape of the beam applied to the patient more closely matches the shape of the target presented to the beam, i.e. the tumour. One form of collimator is a multi-leaf collimator (MLC) comprising an array of moveable leaves that may be positioned to intersect and block parts of the radiation beam so as to define the shape of the radiation beam at the target. WO 2008/141667 discloses MLCs.

It has been proposed to integrate a radiotherapy system with a magnetic resonance imaging (MRI) system to allow the target to be imaged and to provide guidance for the shaping and positioning of the radiation beam to obtain effective treatment. Image guided radiation therapy (IGRT) comprises obtaining an image of the patient that includes the target, and using this image to design a radiotherapy treatment plan involving irradiating the target from different positions around the patient, while adjusting the MLC to obtain an appropriate beam shape at the target for each irradiation direction. Once the treatment plan has been created, the patient is then placed in the IGRT system and irradiation commences. By obtaining further images simultaneously with irradiation, any changes in the shape and location of the target from that in the initial image (for example due to patient movement, growth or shrinkage of the tumour, etc.) can be determined and the beam shape modified by adjustment of the MLC during the treatment so that the applied radiation beam can correspond to that required in the treatment plan. EP 2359905 discloses an IGRT apparatus.

This invention addresses issues in the determination of the beam shape at the target.

SUMMARY OF THE INVENTION

A first aspect provides a method of determining the shape of a radiation beam of a radiotherapy system at a target position, the system comprising a radiation source for projecting the radiation beam towards the target position along a beam axis; and a multi-leaf collimator disposed between the radiation source and the target position, the multi-leaf collimator comprising an array of moveable leaves that may be positioned to intersect and block parts of the radiation beam so as to define the shape of the radiation beam at the target position, wherein at least some of the leaves in the array are aligned such that the planes of those leaves converge at a point that is displaced laterally from the radiation source; the method comprising for each leaf in the array that is positioned to intersect the radiation beam, determining a projected width with respect to the radiation beam, wherein the projected width is greater than the thickness of the respective leaf, and for leaves of substantially the same thickness, determining a wider projected width for a leaf further from the beam axis than the projected width for a leaf closer to the beam axis; and using the projected leaf width to determine the shape of the radiation beam at the target position.

Where all of the leaves of the multi-leaf collimator have substantially the same thickness, the method comprising determining a progressively wider projected width for leaves the further they are from the beam axis.

The method can comprise using the projected leaf width to determine the position of an edge of the radiation beam at the target position.

The projected leaf width can be determined as the distance, in a plane perpendicular to the beam axis and passing through the leaf, between (i) the lateral edge extremity of the leaf furthest from the beam axis in a plane extending through the source, and (ii) a plane extending through the source and including the a lateral edge extremity of the leaf closest to the beam axis.

The target position can be defined for a subject (e.g. a patient) that is moveable into and out of the radiation beam. In this case, the method can further comprise identifying a target position in a subject; determining an initial desired beam shape necessary to irradiate the target position; positioning the subject for irradiation by the radiation beam; positioning the leaves of the multi-leaf collimator based on the initial beam shape at the target position; irradiating the target position with the beam; determining a revised beam shape at the target position; and adjusting the position of one or more leaves of the multi-leaf collimator to change the beam shape from the initial beam shape to the revised beam shape. This method optionally comprises adjusting the position of the radiation source with respect to the subject and irradiating the target position from at least one of different direction, optionally further comprising adjusting the position of the leaves of the multi-leaf collimator to define the shape of the beam at a current irradiation direction to compensate for differences between the initial radiation beam shape at a previous irradiation direction, and the revised radiation beam shape for the current irradiation direction.

The method can comprise storing values of the projected width for each leaf in a lookup table, and consulting the values stored in the lookup table when determining the shape of the radiation beam at the target position.

A further aspect provides radiotherapy system comprising a radiation source for projecting the radiation beam towards a target position along a beam axis; a multi-leaf collimator disposed between the radiation source and the target position, the multi-leaf collimator comprising an array of moveable leaves that may be positioned to intersect and block parts of the radiation beam so as to define the shape of the radiation beam at the target position, wherein at least some of the leaves in the array are aligned such that the planes of those leaves converge at a point that is displaced laterally from the radiation source; and a control system for controlling the multi-leaf collimator to move the leaves to provide a desired beam shape at the target position; wherein the control system is configured to operate the radiotherapy system in accordance with a method according to the first aspect.

All of the leaves of the multi-leaf collimator can have substantially the same thickness.

Another aspect provides a computer-readable medium storing instructions that, when read by a suitably programmed device, provide instructions for performance of a method according to the first aspects.

Further aspects, including methods of treating a patient, and methods of treating tumours are also provided.

BRIEF DESCRIPTION OF THE DRAWINGS

The invention will now be described by way of example with reference to the accompanying drawings, in which.

DETAILED DESCRIPTION OF THE DRAWINGS

Figure 1:
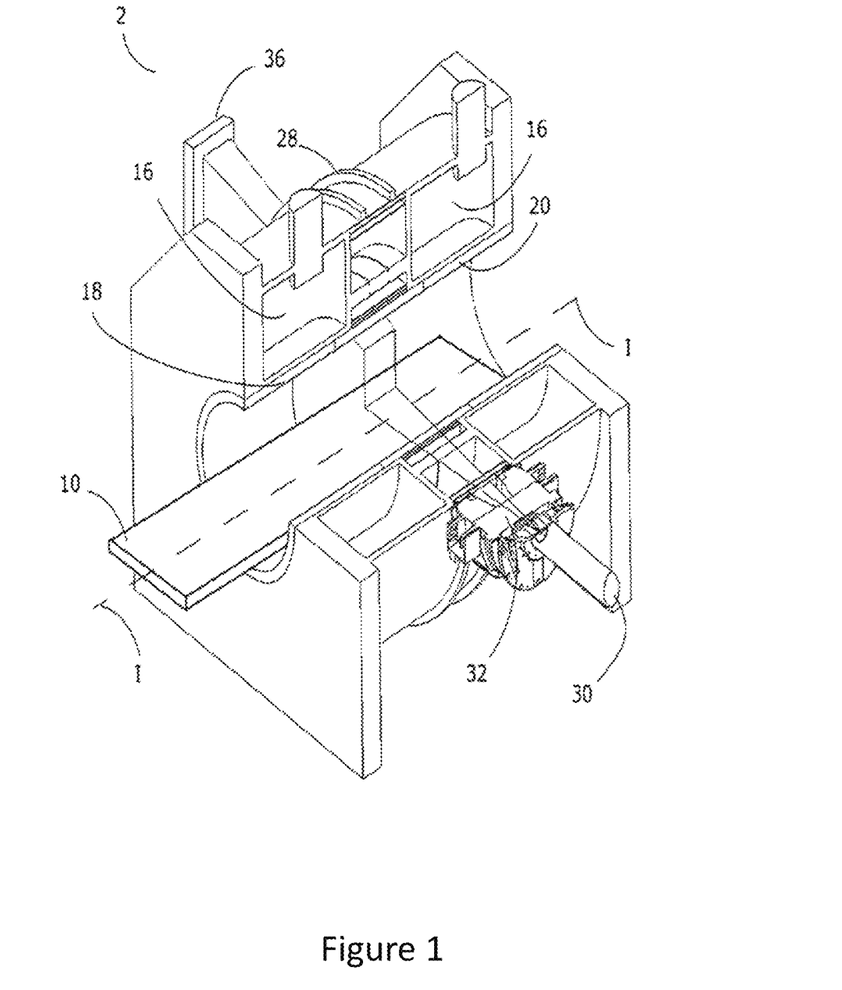
FIG. 1 shows a system comprising a radiotherapy apparatus and a magnetic resonance imaging apparatus.

FIG. 1 shows a system comprising a radiotherapy apparatus and a magnetic resonance imaging (MRI) apparatus of the type described in EP 2359905. The radiotherapy apparatus 6 and MRI apparatus 4 are shown schematically in FIG. 2.

Figure 2:
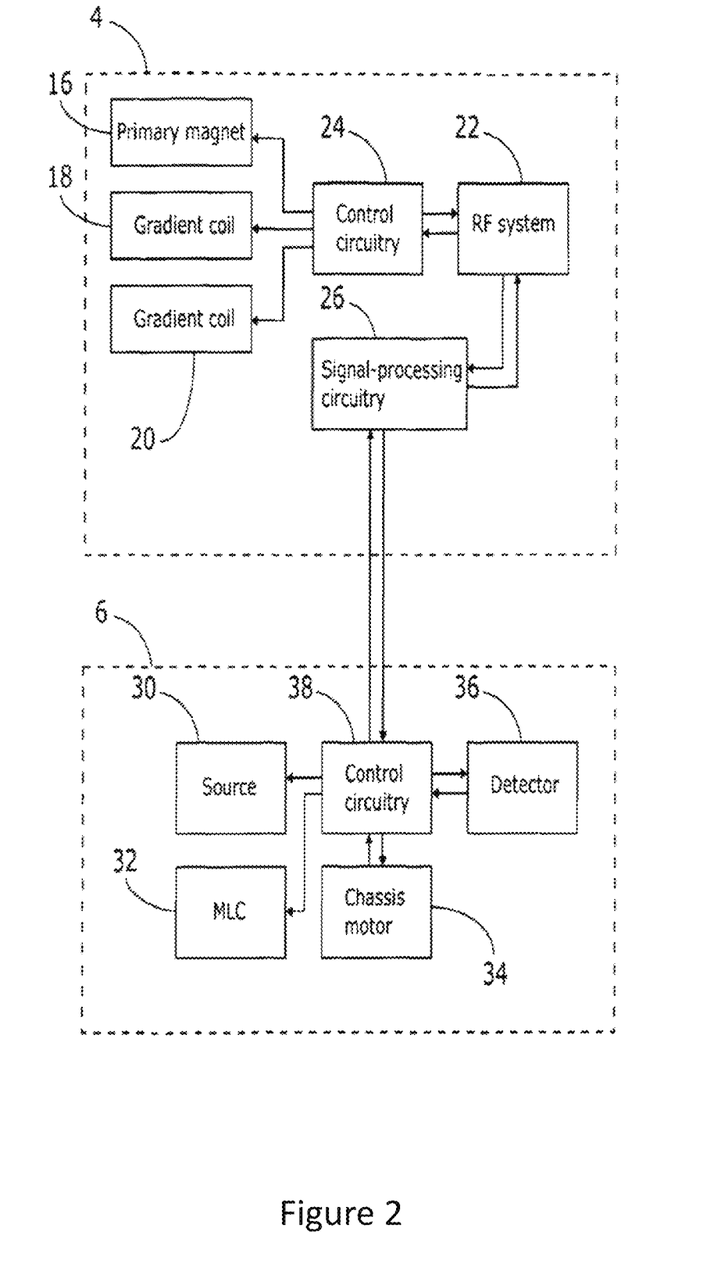
FIG. 2 shows a schematic representation of the system of FIG. 1.

The system includes a couch 10, for supporting a patient in the apparatus. The couch 10 is movable along a horizontal, translation axis (labelled "I"), such that a patient resting on the couch is moved into the radiotherapy and MRI apparatus as described in WO 2009/007737.

The system 2 also comprises an MRI apparatus 4, for producing real-time images of a patient positioned on the couch 10. The MRI apparatus includes a primary magnet 16 which acts to generate the primary magnetic field for magnetic resonance imaging. The magnetic field lines generated by the magnet 16 run substantially parallel to the central translation axis I. The primary magnet 16 comprises one or more coils with an axis that runs parallel to the translation axis I. The one or more coils may be a single coil or a plurality of coaxial coils of different diameter, as illustrated. The coil(s) in the primary magnet 16 is arranged such that a central window of the magnet 16 is free of coils. The magnet 16 may further comprise one or more active shielding coils, for generating a magnetic field outside the magnet 16 of approximately equal magnitude and opposite polarity to the primary magnetic field. The more sensitive parts of the system 2, such as the accelerator, are positioned in this region outside the magnet 16 where the magnetic field is cancelled, at least to a first order. The MRI apparatus 4 further comprises two gradient coils 18, 20, which generate the gradient magnetic field that is superposed on the primary magnetic field. These coils 18, 20 generate a gradient in the resultant magnetic field that allows spatial encoding of the protons so that their position can be determined from the frequency at which resonance occurs (the Larmor frequency). The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system 22 transmits radio signals at varying frequencies towards the patient, and detects the absorption at those frequencies so that the presence and location of protons in the patient can be determined. The RF system 22 may include a single coil that both transmits the radio signals and receives the reflected signals, dedicated transmitting and receiving coils, or multi-element phased array coils, for example. Control circuitry 24 controls the operation of the various coils 16, 18, 20 and the RF system 22, and signal-processing circuitry 26 receives the output of the RF system, for generating images of the patient supported by the couch 10.

The system 2 further comprises a radiotherapy apparatus 6 which delivers doses of radiation to a patient supported by the couch 10. The majority of the radiotherapy apparatus 6, including at least a source of radiation 30 (e.g. an x-ray source) and a multi-leaf collimator (MLC) 32, is mounted on a chassis 28. The chassis 28 is continuously rotatable around the couch 10 when it is inserted into the treatment area, powered by one or more chassis motors 34. In the illustrated embodiment, a radiation detector 36 is also mounted on the chassis 28 opposite the radiation source 30 and with the rotational axis of the chassis positioned between them. The radiotherapy apparatus 6 further comprises control circuitry 38, which may be integrated within the system 2 shown in FIG. 1 or remote from it, and controls the source the radiation source 30, the MLC 32 and the chassis motor 34.

The radiation source 30 is positioned to emit radiation through the window defined by the two gradient coils 18, 20, and also through the window defined in the primary magnet 16. The source 30 emits a divergent beam of radiation. The radiation beam is collimated to a rounded corner rectangular section with appropriate shielding prior to arrival at the MLC 32. The radiation beam is relatively narrow in the axial direction, and is relatively wide in azimuthal direction (both with respect to the axis of rotation of the chassis). Thus, the beam takes a "fan" shape that is suited to the geometry of the system 2, in which two gradient coils 18, 20 are displaced from one another in order to allow the radiation access to the patient. A fan-shaped beam provides substantial radiation to the patient through the narrow window, meaning that the gradient coils 18, 20 can be placed closer together than with conventional integrated radiotherapy/imaging systems. This allows the gradient coils 18, 20 to generate stronger gradient fields than would otherwise be the case, increasing the quality of the images obtained by the MRI apparatus 4.

The radiation detector 36 is configured for the geometry shown in FIG. 1, and can be used for imaging and daily calibration. The detector 36 is positioned outside the magnetic coils 16, 18, 20 on the chassis 28, aligned with the radiation beam exit. It therefore has a fixed position relative to the radiation source 30 and MLC 32.

In operation, an MRI image is obtained of the patient, including the desired target region (e.g. a tumour). On the basis of this image, a treatment plan is designed that includes irradiating the target region from a number of different directions, with the beam shape defined for each irradiation direction so as to fully irradiate the target region while limiting irradiation of healthy tissue as much as possible. Subsequently, a patient is placed on the couch 10 and the couch is inserted into the treatment area defined by the magnetic coils 16, 18 and the chassis 28. The control circuitry 38 controls the radiation source 30, the MLC 32 and the chassis motor to deliver radiation to the patient through the window between the coils 16, 18. The control circuitry 38 controls the source to deliver radiation in a fan beam, in the usual pulsed manner. The chassis motor 34 is controlled such that the chassis 28 rotates about the patient, meaning the radiation can be delivered from different directions. The MLC 32 is controlled to take different shapes, thereby altering the shape of the beam that reaches the patient. Simultaneously with rotation of the chassis 28 about the patient, the couch 10 may be moved along a translation axis into or out of the treatment area (i.e. parallel to the axis of rotation of the chassis).

The MRI apparatus 4, and specifically the signal-processing circuitry 26, delivers images of the patient in real-time (or near real-time with a delay in the order of milliseconds) to the control circuitry 38. This information allows the control circuitry to adapt the operation of the source 30, MLC 32 and/or chassis motor 34, such that the radiation delivered to the patient accurately tracks the motion of the patient, for example due to breathing.

Figure 3:
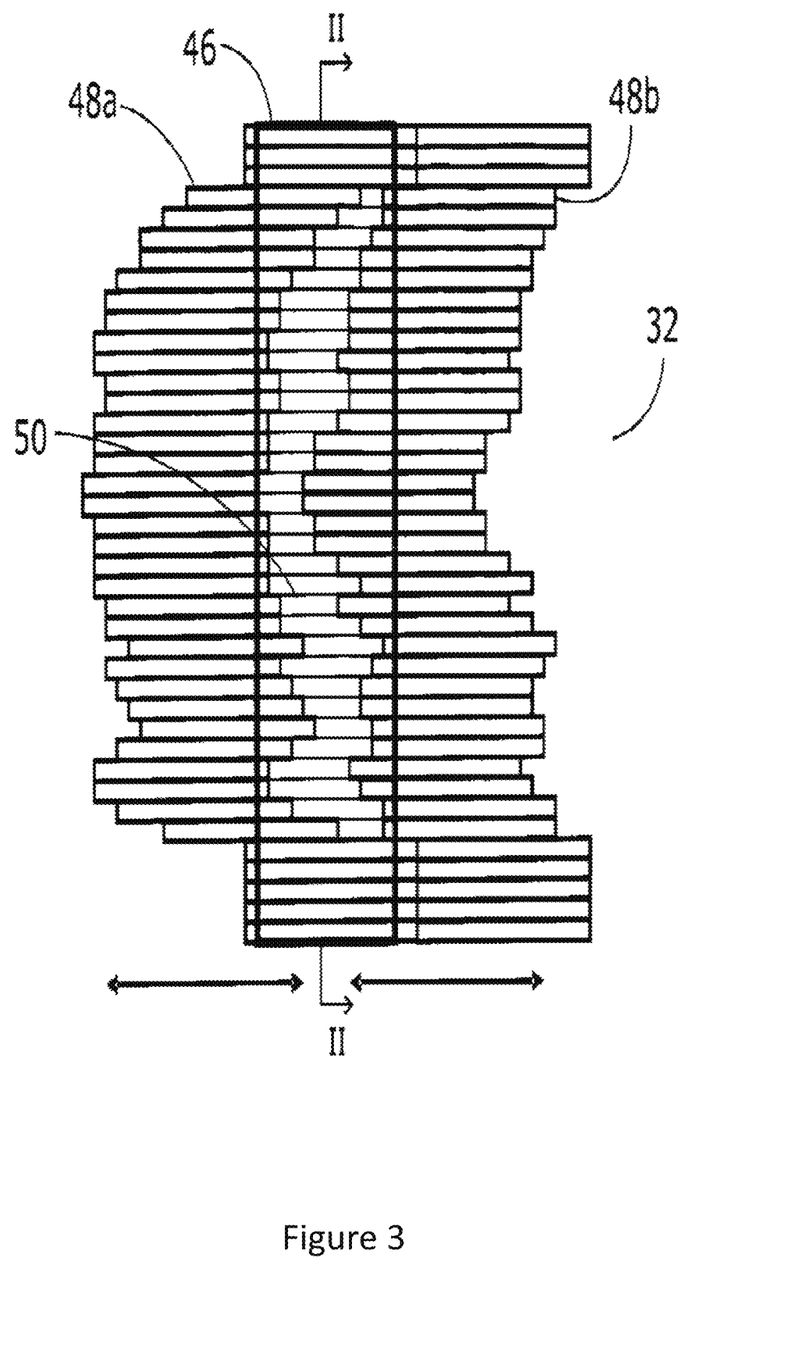
FIG. 3 shows a multi-leaf collimator.

FIG. 3 shows an MLC 32 comprising a housing 46 which is effectively shaped as an elongate rectangular aperture. Pairs of leaves (for example as indicated with reference numerals 48a, 48b) are located along the housing 46, and are movable into and out of the aperture in a substantially continuous number of positions by action of a plurality of actuators. The actuators may be operated by electromagnetic motors, placed outside the coils 16, 18, 20 to minimize interference with the magnetic fields present in the MRI apparatus 4. At one extreme, each leaf may be positioned entirely outside the aperture; at the other, each leaf may be positioned entirely within the aperture. As illustrated, each leaf may be separately controllable to move into and out of the housing (i.e. the movement of the leaves in each pair is not linked). This embodiment allows the target position to be tracked more accurately, as it does not assume that the target is in the centre of the field of view.

The leaves are manufactured from a dense material with a relatively high atomic number (e.g. tungsten) and represent a considerable barrier to the radiation due to their relatively thick cross section along the beam axis.

The leaves are sheet-like structures having a width defined by the physical dimension along a minor axis that lies orthogonal to the major axes of the sheet. The thickness can be considered to be is the maximum physical width.

The projected width of the leaf is the width dimension of the portion of the beam occluded by the leaf at the furthest point of the leaf from the source. The projected width will depend upon the angle of alignment of the leaf with respect to the direction of projection of the beam.

The leaves 48 move only in the longitudinal direction. This makes the leaves short as they only have to traverse the small dimension of the collimator 32. As they are only moving a small distance the tip of each leaf can have a large radius and thereby minimize the radiation penumbra. Also, moving in this direction facilitates target tracking as targets generally move due to breathing and this is in a predominantly longitudinal direction.

Because the leaves 48 are relatively thin compared to the beam width, and because the MLC is relatively far from the target region/treatment location, the shadow from a leaf can be significantly wider than the physical width of the leaf.

All of the leaves 48 of the MLC can have the same (maximum) thickness. While the leaves at or near the beam axis provide a relatively consistent shadow, the leaves further from the beam axis need to be angled to accommodate the divergence of the beam while projecting the same shadow, the angle becoming progressively greater the further from the beam axis a leaf is positioned. For example, the centre of each leaf is positioned on a common line and the leaves progressively angled to achieve this effect.

Figure 4A:
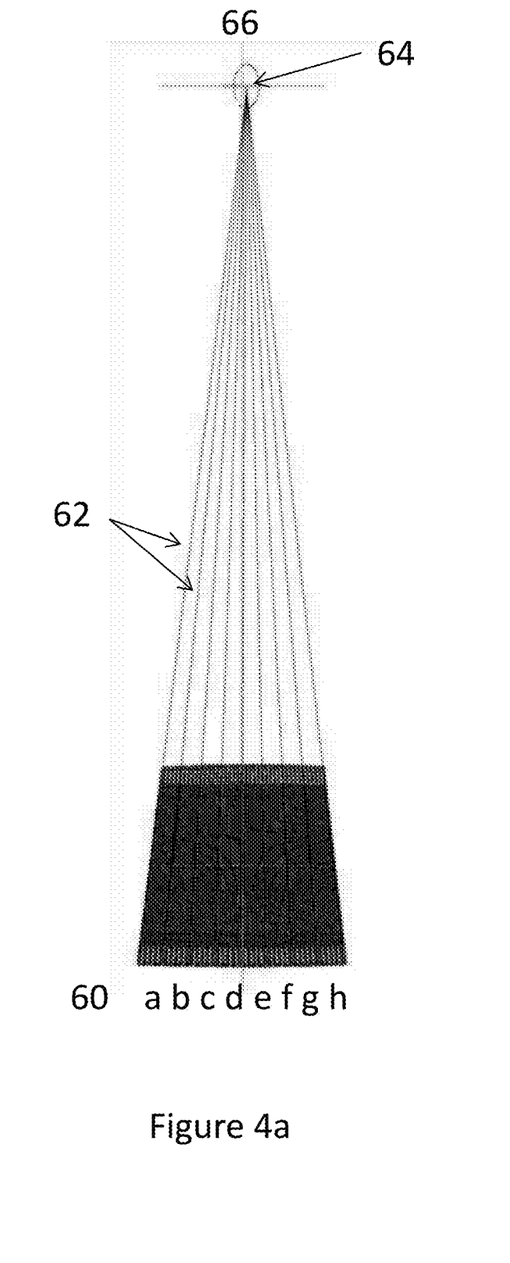
FIGS. 4a and 4b show the alignment of leaves in the MLC of FIG. 3.
Figure 4B:
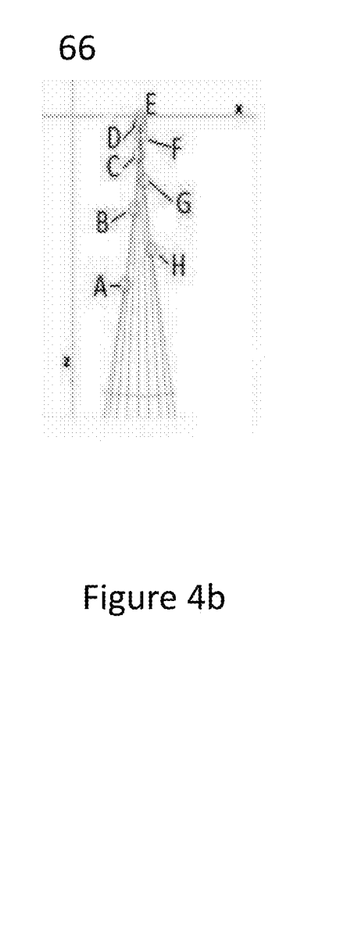

A small air gap is also present between each pair of leaves in order to allow movement relative to each other. This air gap provides a potential unobscured path from the source to the target region, even when the leaves are positioned to block the beam. To avoid this open path, the leaves are defocused from the beam source. Instead of each leaf being aligned with the source, the leaves are aligned on a point laterally displaced from the source by a small distance. More than one defocused point can be used, for example, each leaf being focused on a different point that it spaced a small distance laterally (x direction) from and in a direction (z direction) parallel to the beam axis. For example, for an MLC with 80 leaves, each leaf can focus on a separate point that is 2.0-4.0 mm in the x direction and 0.0-6.0 mm in the z direction from the source. FIGS. 4a and 4b shows an example of such a defocused array of leaves in an MLC. The array 60 comprises 80 leaves. For ease of understanding, these are indicated in eight groups 60a-60h. The ray traces 62 for each group to the focus of the leaves 64 is shown. FIG. 4b shows the foci in detail relative to the beam axis 66. As can be seen, each group 60a-60h has a different focus, A-H, each being displaced laterally (x direction) and parallel to the beam axis 66 (z direction). As will be appreciated, if each leaf has a different defocussing, there will be a separate focus for each leaf, the points A-H serving to illustrate how the focus may vary from leaf to leaf.

Figure 5:
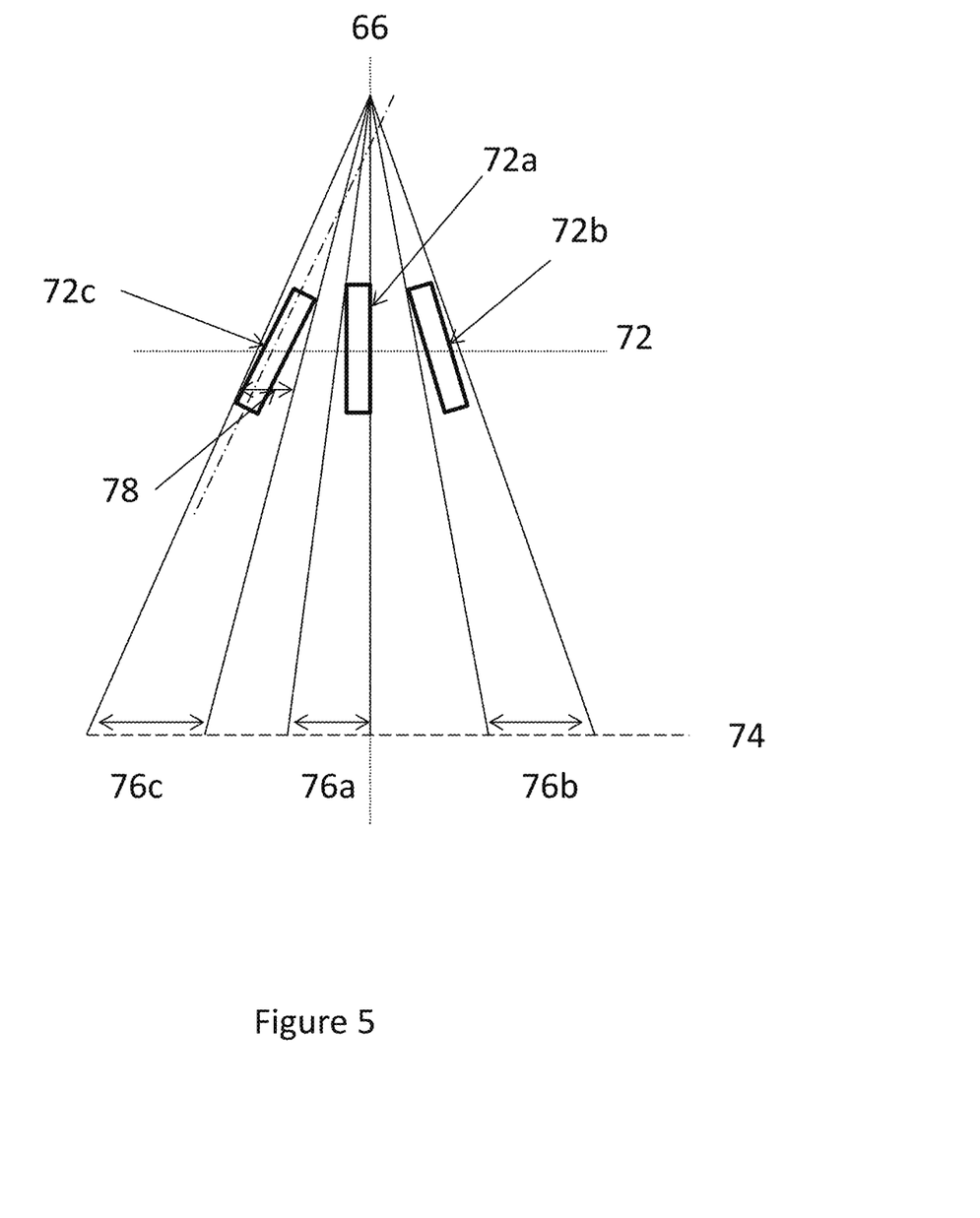
FIG. 5 shows a schematic illustration of the effect of leaf alignment in the MLC.

The angling of the leaves and the defocusing has an effect on the shadow cast by each individual leaf. FIG. 5 shows a schematic view of the MLC array illustrating this effect, for simplicity illustrating the optical leaf edge projections. FIG. 5 shows the relative arrangement of the source 70, the MLC 72 (showing only three leaves 72a, 72b, and 72c, each having the same maximum width), and the target region, here represented as a flat surface 74. Leaf 72a is close to the beam axis 66 and produces a shadow 76a at the target region 74. Leaf 72b is shown further from the beam axis 66 and angled to face the source 70 (this arrangement is shown for illustrative purposes and may not be present in a complete array). Because of the divergent nature of the beam, the shadow 76b produced at the target region 74 is wider than that of leaf 72a. Leaf 72c is a similar distance from the beam axis 66 as leaf 72b, but is defocused so as to align with a point 64 that is laterally displaced to one side of the source 70. This leads in turn to an even wider shadow 76c at the target region 74. While the treatment regions 74 is shown as a flat surface in FIG. 5, in practice it will be a tumour having a non-planar surface defining a volume (the tumour volume).

Figure 6:
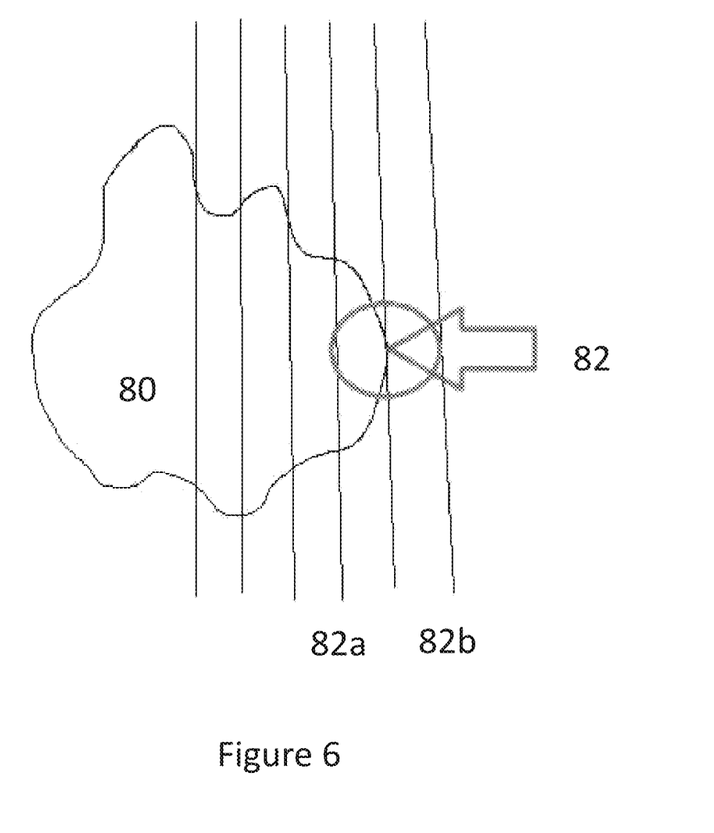
FIG. 6 shows a schematic representation of a treatment region and beam edge.

In treatment planning, one important factor is to be able to determine the position of the edge of the beam at the target region. FIG. 6 illustrates this schematically. For treatment of a target tumour 80, one important aspect is determine whether or not the edge 82 of the treatment beam is accurately positioned at the edge of the tumour 80. If the beam edge is at position 82a, the tumour is under-treated. Conversely, if the beam edge is at position 82b, healthy tissue is also irradiated unnecessarily. As is discussed above, while the shape and position of tumour 80 might have been known in an initial image, the size, shape, and position may change up to a during radiotherapy treatment, meaning that the MLC will need to be reconfigured accordingly.

Figure 7A:
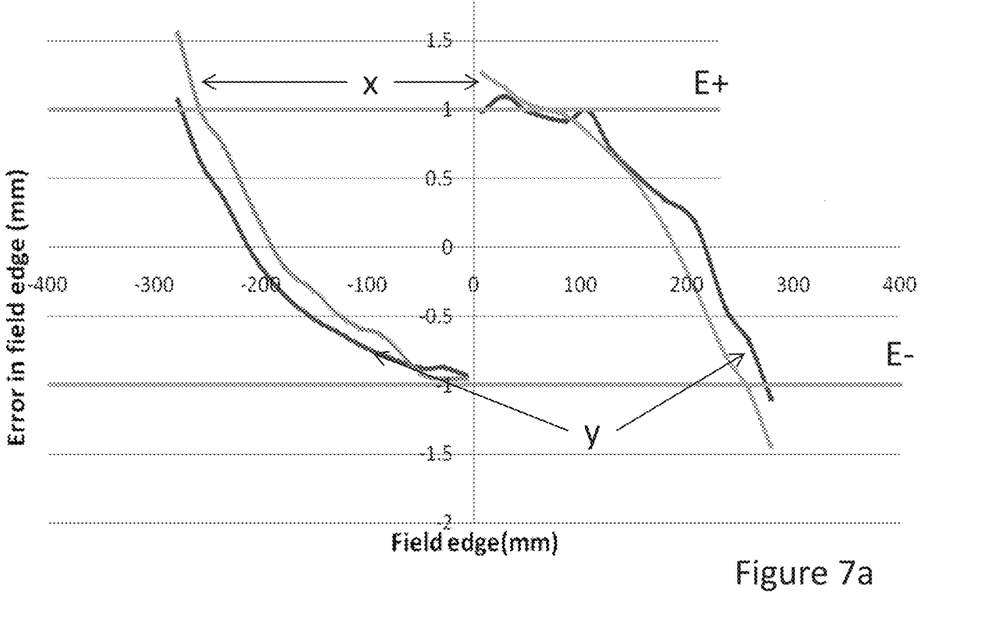
FIGS. 7a and 7b show plots of error in field edge position vs distance from beam axis for different leaf widths.

Certain previous treatment planning systems have worked on the basis of the actual leaf width (i.e. the same physical width of each leaf in the array) to determine the edge position. In many cases, this is a valid assumption as the difference in shadow widths 76a, 76b, and 76c are within acceptable tolerances for beam shape determination. However, this difference is magnified where the MLC is relatively close to the source, but relatively far from the treatment region, such as in the arrangement shown in FIG. 1. FIG. 7a illustrates error in the edge position (y axis) vs. distance from beam axis (x axis) from a model using a fixed width for the MLC leaves. The error is similar whether using simple ray tracing from the source to the edge of the leaf (line x), or when using Monte Carlo modelling to account for scatter (line y). Lines E+ and E− provide an example of possible limits of acceptable error for the system. As can be seen, the edge errors at the extremes, as well as near the beam axis, can exceed these limits.

Figure 7B:
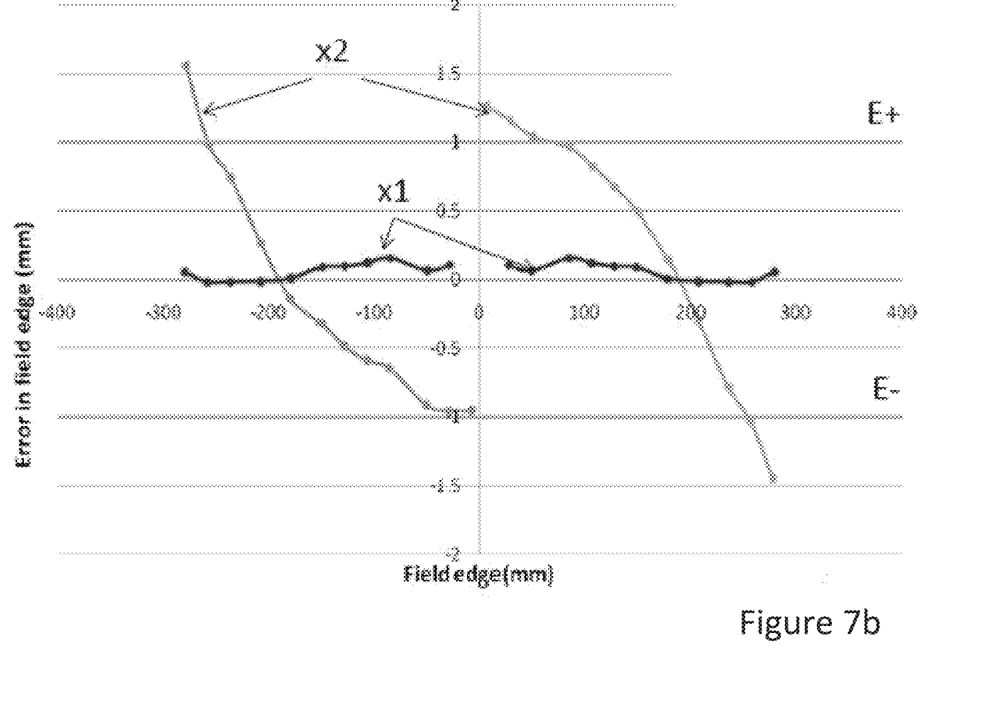

In the present method, instead of using the same width for each leaf in the MLC, the beam shape is determined using the surface projected to the beam by each leaf (the "projected" width, 78 of FIG. 5). The projected width can be determined for each leaf in the array. For example, the projected leaf width can be determined as the distance, in a plane perpendicular to the beam axis and passing through the leaf, between (i) the lateral edge extremity of the leaf furthest from the beam axis in a plane extending through the source, and (ii) a plane extending through the source and including the a lateral edge extremity of the leaf closest to the beam axis. As the separation and alignment of the source and the MLC is fixed, the projected width will be essentially constant. Therefore, one approach is to determine the projected width for each leaf and store it in a look-up table in the treatment planning system. Using this approach leads to the edge errors shown in FIG. 7b which shows a comparative plot to that in FIG. 7a and compares the ray trace edge error using a fixed leaf width (line x2, corresponding to line x of FIG. 7a), with the corresponding edge error using the projected width for each leaf (line x1), In this case, the edge errors lie well within the limits E+ and E−.

Dose calculation is often based on the computation of leaf boundary values (LBVs). LBVs are used to describe somehow how the edge of a leaf affects the penumbra of a field that is collimated by the respective edge. There is no LBV per leaf edge, instead a single value is used for the two common edges of adjacent leaves (hence the term "boundary"). To determine this experimentally, for example, one would take profiles of a field that has leaves 1-5 open and leaves 6-80 closed, and look for the 50% penumbra point (also known as the "radiation field edge"). Then one would look for the 50% point for the complementary field (leaves 1-5 closed and 6-80 open), The average of the two radiation field edges at the isocenter is the leaf boundary for leaves 5 and 6. Then the dose calculation takes this LBV and uses it to create a model of the two leaf edges.

To determine the projected width 78 of a leaf 72 theoretically, one has to choose the particular ray that starts at the source and traverses the edge of the leaf such that it is attenuated by 50%. That ray has to travel through the leaf by exactly the 50% attenuation length for that particular energy spectrum.

Due to the slight defocusing, one of the 50% rays will cut the top corner (source side) of one of the leaves, while the other will cut the bottom corner (patient side) of the other leaf. There is a symmetry in this: the amount by which the first 50% ray cuts the upper corner of one leaf equals approximately the amount by which the second 50% ray cuts the lower corner of the second leaf. The two rays considered for averaging are almost parallel. Thus instead of the rays that correspond to the 50% radiation attenuation one can use with good precision the rays as given by the optical field (as shown in FIG. 5). Another alternative is to use the rays that pass through the middle of the leaf edge face (middle in the vertical direction). All of these approaches result in essentially the same value for the LBV, any differences being smaller than would be measurable for radiation field profiles or film.

In certain implementations, the general symmetry of the MLC leaves about a central leaf boundary is used to reduce the processing burden when determining a projected width for all the leaves with respect to the radiation beam. The central leaf boundary is the boundary formed at the two common edges of adjacent central leaves of the MLC. This central boundary may be described as the closest leaf boundary to the beam axis. The remaining leaf boundaries then fall into one of two groups: a first group located on a first side of the central leaf boundary, and a second group locating on a second, opposing side of the central leaf boundary. For example, with reference to FIG. 5, leaf 72b would form leaf boundaries which fall into the first group, while leaf 72c would form boundaries which fall into the second group.

Using the methods disclosed herein, it is possible to determine the LBV for each leaf boundary in the first group, i.e. on one side of the central boundary, and thus to determine the projected width for the leaves on that side of the MLC using the methods disclosed herein. Because all of the leaves of the multi-leaf collimator have substantially the same thickness, due to the symmetry of the MLC about the central leaf boundary it is then possible to assign LBVs for the leaves in the second group, i.e. on the other, opposing side of the central leaf boundary by essentially mirroring the leaf boundary values about the beam axis 66. In other words, the LBVs for the first, second and third LBVs closest to the central leaf boundary in the first group may correspond with the LBVs for the first, second and third closest LBVs closest to the central leaf boundary in the second group, and so on. This approach is a useful approximation for implementations where all of the leaves of the multi-leaf collimator have substantially the same thickness. This method reduces not only the processing power required but also the time required to build the model, while producing results within acceptable margins for error.

In other implementations, the set of LBVs may instead be slightly asymmetric with respect to the isocenter position and/or the beam axis as the defocusing of the central leaves shared surface breaks the symmetry of the model. In other words, in an alternative implementation to that described above, the LBV for each boundary is determined independently and separately from the other LBV determinations and does not rely on symmetry about a central leaf boundary position to provide an approximation. This approach advantageously increases the accuracy of the model.

In all other respects, the system can be operated in the same manner as before. The look up table is a relatively quick and simple way to provide the improved estimation of leaf width that allows the initial and revised MLC configurations to be set in accordance with the instructions from the treatment planning system.

Various changes can be made to the methods and systems described above within the scope of the invention.

The invention claimed is:

1. A method of determining a shape of a radiation beam at a target position of a radiotherapy system, the system comprising:
a radiation source for projecting the radiation beam towards the target position along a beam axis; and
a multi-leaf collimator disposed between the radiation source and the target position, the multi-leaf collimator comprising a defocused array of moveable leaves configured to be positioned to intersect and block a part of the radiation beam so as to define the shape of the radiation beam at the target position, each leaf having a plane extending through a plane perpendicular to the beam axis and a width extending in a direction perpendicular to the plane of the respective leaf, wherein at least a first leaf and a second leaf are aligned such that the plane of the first leaf converges with the plane of the second leaf at a line, wherein a point within the line is displaced laterally from the beam axis;
the method comprising:
determining a projected width, with respect to the radiation beam, for each leaf positioned to intersect the radiation beam, the projected width being greater than a width of the respective leaf, wherein the determined projected width for a leaf further from the beam axis is wider than the determined projected width for a leaf closer to the beam axis;
determining the shape of the radiation beam at the target position using the projected width of at least one leaf;
positioning the leaves of the multi-leaf collimator based on the determined shape of the radiation beam; and
irradiating the target position with the beam.

2. The method as claimed in claim 1, wherein all of the leaves of the multi-leaf collimator have substantially the same width, the method comprising:
determining a progressively wider projected width for a leaf as a distance between the leaf and the beam axis increases.

3. The method as claimed in claim 1, comprising:
determining the position of an edge of the radiation beam at the target position using the projected width of at least one leaf.

4. The method as claimed in claim 1, wherein the projected width is determined as a distance, in the plane perpendicular to the beam axis and passing through the leaf, between (i) a lateral edge extremity of the leaf furthest from the beam axis in a plane extending through the radiation source, and (ii) a plane extending through the radiation source and including a lateral edge extremity of the leaf closest to the beam axis.

5. The method as claimed in claim 1, comprising:
storing values of the projected width for each leaf in a lookup table, and
consulting the values stored in the lookup table when determining the shape of the radiation beam at the target position.

6. The method as claimed in claim 1, wherein the target position is defined for a subject that is moveable into and out of the radiation beam.

7. The method as claimed in claim 6, further comprising:
identifying a target position in the subject;
determining an initial desired beam shape to irradiate the target position;
positioning the subject for irradiation by the radiation beam;
positioning the leaves of the mufti-leaf collimator based on the initial beam shape at the target position;
irradiating the target position with the beam;
determining a revised beam shape at the target position; and
adjusting the position of one or more leaves of the multi-leaf collimator to change the beam shape from the initial beam shape to the revised beam shape.

8. The method as claimed in claim 7, wherein the radiation source is at a first position when the initial beam is determined and at a second position when the revised beam shape is determined, the first position being different from the second position.

9. A radiotherapy system comprising:
a radiation source for projecting the radiation beam towards a target position along a beam axis;
a multi-leaf collimator disposed between the radiation source and the target position, the multi-leaf collimator comprising a defocused array of moveable leaves configured to be positioned to intersect and block a part of the radiation beam so as to define the shape of the radiation beam at the target position, each leaf having a plane extending through a plane perpendicular to the beam axis and a width extending in a direction perpendicular to the plane of the respective leaf, wherein at least a first leaf and a second leaf are aligned such that the plane of the first leaf converges with the plane of the second leaf at a line, wherein a point within the line is displaced laterally from the beam axis; and
a control system for controlling the multi-leaf collimator to move the leaves to provide a desired beam shape at the target position;
wherein the control system is configured to:
determine a projected width, with respect to the radiation beam, for each leaf positioned to intersect the radiation beam, the projected width being, greater than a width of the respective leaf, wherein the determined projected width for a leaf further from the beam axis is wider than the determined projected width for a leaf closer to the beam axis;
determine the shape of the radiation beam at the target position using, the projected width of at least one leaf;
position the leaves of the multi-leaf collimator based on the determined shape of the radiation beam; and
irradiate the target position with the beam.

10. The system as claimed in claim 9, wherein all of the leaves of the mufti-leaf collimator have substantially the same width.

11. The system as claimed in claim 9, wherein the control system is configured to:
determine a progressively wider projected width for a leaf as a distance between the leaf and the beam axis increases.

12. The system as claimed in claim 9, wherein the control system is configured to:
determine the position of an edge of the radiation beam at the target position using the projected width of at least one leaf.

13. The system as claimed in claim 9, wherein the projected width is determined as a distance, in the plane perpendicular to the beam axis and passing through the leaf, between (i) a lateral edge extremity of the leaf furthest from the beam axis in a plane extending through the radiation source, and (ii) a plane extending through the radiation source and including a lateral edge extremity of the leaf closest to the beam axis.

14. The system as claimed in claim 9, wherein the control system is configured to:
   store values of the projected width for each leaf in a lookup table, and
   consult the values stored in the lookup table when determining the shape of the radiation beam at the target position.

15. The system as claimed in claim 9, wherein the target position is defined for a subject that is moveable into and out of the radiation beam.

16. The system as claimed in claim 15, wherein the control system is configured to:
   identify a target position in the subject;
   determine an initial desired beam shape to irradiate the target position;
   position the subject for irradiation by the radiation beam;
   position the leaves of the multi-leaf collimator based on the initial beam shape at the target position;
   irradiate the target position with the beam;
   determine a revised beam shape at the target position; and
   adjust the position of one or more leaves of the multi-leaf collimator to change the beam shape from the initial beam shape to the revised beam shape.

17. The system as claimed in claim 16, wherein the radiation source is at a first position when the initial beam is determined and at a second position when the revised beam shape is determined, the first position being different from the second position.

* * * * *